(12) United States Patent
Toms et al.

(10) Patent No.: US 8,292,861 B2
(45) Date of Patent: Oct. 23, 2012

(54) OVERLABEL WRAPPER FOR ABSORBENT ARTICLES

(75) Inventors: Douglas Toms, Cincinnati, OH (US);
Jeremy Robert Basham, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 310 days.

(21) Appl. No.: 12/695,582

(22) Filed: Jan. 28, 2010

(65) Prior Publication Data

US 2011/0184367 A1 Jul. 28, 2011

(51) Int. Cl.
*A61F 13/15* (2006.01)
*A61L 15/00* (2006.01)

(52) U.S. Cl. ......... 604/385.02; 604/385.03; 604/385.01; 206/440; 206/438

(58) Field of Classification Search ............. 604/385.02, 604/385.03, 385.01; 206/440, 438, 484
See application file for complete search history.

(56) References Cited

U.S. PATENT DOCUMENTS

| | | | |
|---|---|---|---|
| 6,010,001 A | 1/2000 | Osborn | |
| 6,024,732 A | 2/2000 | Samuelsson | |
| 6,037,281 A | 3/2000 | Mathis et al. | |
| 6,716,203 B2 | 4/2004 | Sorebo et al. | |
| 7,073,666 B2 | 7/2006 | Arndt | |
| 7,422,105 B2 | 9/2008 | Loyd et al. | |
| 7,553,302 B2 | 6/2009 | Bechyne et al. | |
| 2003/0065300 A1 | 4/2003 | Suga | |
| 2003/0065302 A1 | 4/2003 | Kuroda et al. | |
| 2005/0098466 A1 | 5/2005 | Thomas | |
| 2005/0131370 A1 | 6/2005 | Hantke et al. | |
| 2007/0156109 A1 | 7/2007 | Loyd et al. | |
| 2009/0069770 A1 | 3/2009 | Drevik et al. | |
| 2009/0232425 A1 | 9/2009 | Tai et al. | |
| 2010/0249742 A1 | 9/2010 | McConnell et al. | |

FOREIGN PATENT DOCUMENTS

| | | |
|---|---|---|
| EP | 1490008 B1 | 6/2009 |
| JP | 2001/159063 | 6/2001 |
| WO | WO-9623711 A1 | 8/1996 |

OTHER PUBLICATIONS

U.S. Appl. No. 12/695,590, filed Jan. 28, 2010, Douglas Toms, et al.
PCT International Search Report dated Apr. 8, 2011, 4 pages.

*Primary Examiner* — Jacqueline F. Stephens
(74) *Attorney, Agent, or Firm* — Andrew J. Hagerty; Amanda T. Barry

(57) ABSTRACT

An individually packaged absorbent article including an absorbent article and a package. The package can enclose the absorbent article and can have an outer surface and an inner surface. In certain embodiments, the package can include a package material that is a polymeric film. The package can have two opposing faces, and an opening area. The opening area can be provided substantially on a face of the package, and the package having an overlabel substantially covering the opening area.

19 Claims, 3 Drawing Sheets

OVERLABEL WRAPPER FOR ABSORBENT ARTICLES

FIELD OF THE INVENTION

This invention relates to wrappers for individual absorbent articles, and more particularly, to overlabel wrappers for absorbent articles.

BACKGROUND OF THE INVENTION

Absorbent articles, such as absorbent articles for feminine hygiene, are generally used to absorb body exudates, such as menstrual or other body fluids. Certain types of absorbent articles, such as, for example, sanitary napkins, tampons, incontinence pads, and similar articles can be individually packaged. These individual packages can protect the article and can facilitate hygiene, ease of use and identification, and ease of carrying.

Currently available individual packages can have one or more drawbacks. For example, current individual packages can be noisy during carrying and use, which can be undesirable for a discreet user experience. In addition, some packages may not adequately conceal the absorbent article. Furthermore, such packages can feel thin or flimsy, and can have reduced durability and/or can provide a perception of a lower quality product.

Typically, individual packages can be formed from a plastic film, which can protect the absorbent article while providing a smooth and/or shiny outer surface, or formed from paper, which can be biodegradable and easy to open. Both plastic film and paper packages, however, can be noisy. In addition, paper packages can tear and/or become soiled during carrying and use. Other individual packages can include an exterior nonwoven layer that may provide a soft package. The nonwoven exterior of such packages, however, may become soiled during carrying and use, and may not provide a desirable smooth and/or shiny appearance.

Furthermore, many individual packages are opened by tearing or separating the wrapper film or paper, which can be noisy. A noisy wrapper experience can be embarrassing for the user in a public restroom, because others may know that she is using a feminine hygiene device. In addition, tearing or separating the wrapper film or paper can result in a used wrapper that cannot be resealed to cover the used applicator for disposal. This can lead to a messy disposal experience and/or can lead the user to wrap the used applicator in tissue for disposal.

As such, it would be desirable to provide an individual package for an absorbent article that can have improved quietness, softness, an improved opening feature, and/or an improved disposal feature.

SUMMARY OF THE INVENTION

An individually packaged absorbent article including an absorbent article and a package is provided. The package can enclose the absorbent article and can have an outer surface and an inner surface. In certain embodiments, the package can include a package material that is a polymeric film. The package can have two opposing faces, and an opening area that can be provided substantially on a face of the package. The package can also have an overlabel at least partially covering the opening area.

Also provided is an individually packaged absorbent article including an absorbent article and a package enclosing the absorbent article. The package can have an outer surface and an inner surface disposed opposite the outer surface, a periphery, a longitudinal axis, a transverse axis, a length measured parallel to the longitudinal axis, a width measured parallel to the transverse axis, a top, a bottom, and two sides. The package can include a package material having a first component that is a polymeric film. The package can have permanent seals at the top, bottom, and at least one side. In addition, the package can have two opposing faces and an opening area. The opening area can be provided substantially on a face of the package, and the package can have an overlabel at least partially covering the opening area.

Further provided is an individually packaged absorbent article including an absorbent article and a reclosable package enclosing the absorbent article. The package can have an outer surface and an inner surface disposed opposite the outer surface and can include a package material having a first component that is a printed polyolefin film, and a second component that is an absorbent material. The first component and the second component can be joined together to form the package material, and the package material can be oriented such that the first component forms the outer surface of the package and the second component forms the inner surface of the package. The package can have two opposing faces and an opening area. In certain embodiments, the opening area can be provided substantially on a face of the package, and the package can have an overlabel at least partially covering the opening area.

DETAILED DESCRIPTION OF THE INVENTION

Figure 1:
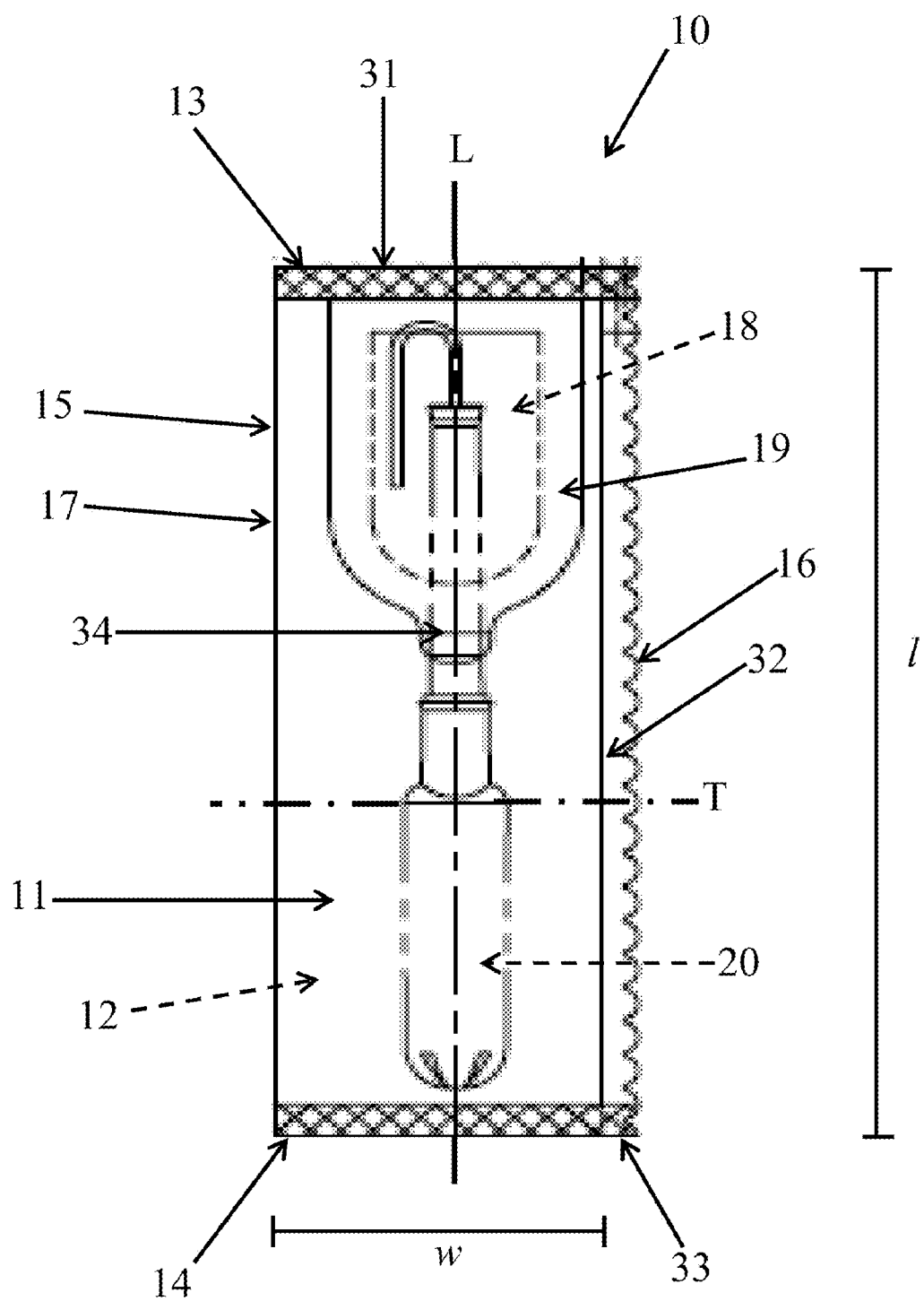
FIG. 1 is a plan view of an individual package.

The present invention relates to individual packages for absorbent articles, such as, e.g., absorbent articles for feminine hygiene. The individual packages can include an opening area in a size suitable for removal of the absorbent article from the package, the opening area being provided substantially on a single face of the package, such as, for example, the front face or the back face of the package. The package can have an overlabel substantially covering the opening area. The overlabel is at least partially releasably attached to the package, such that the overlabel can be partially or entirely removed by a user to reveal the opening and withdraw the absorbent article from the wrapper. In certain embodiments, the overlabel can be partially permanently attached and partially releasably attached to the package.

In addition, in certain embodiments, the individual packages can include a package material that can provide a liquid impermeable exterior and an absorbent interior. For example, in certain embodiments, the package material can have a first component that is a polymeric film and a second component that is an absorbent material. In addition, the package material can be oriented such that the film component forms the exterior of the package and the absorbent component forms the inside of the package. In certain embodiments, the overlabel can be suitable for sealing the used article within the package.

Such packages can provide an easier and quieter opening and use experience for a user. In addition, such packages can provide for improved disposal of a used applicator, such as, for example, by being resealable. Furthermore, when a multiple component packaging material is used, the film outer layer and absorbent material inner layer can provide a quieter, softer package that can provide benefits of a plastic wrapper, such as, e.g., a liquid permeable exterior and a smooth and/or glossy surface that can be amenable to high contrast printing. In addition, such package material can provide a thick and/or cushioned feel and/or improved concealment of an absorbent article contained therein. Furthermore, in certain embodiments, the absorbent interior can absorb or entrap body fluid from a used article and thus can provide for a cleaner disposal experience.

As used herein, the term "absorbent" refers to materials that can hold, retain, entrap, and/or contain body fluids.

As used herein, the term "absorbent article" refers to devices that absorb and contain body exudates, and more specifically, refers to devices that are placed against or in proximity to the body of the wearer to absorb and contain various exudates discharged from the body.

Absorbent articles include, for example, sanitary napkins, incontinence articles, interlabial pads, tampons, and pantyliners.

The term "disposable" is used herein to describe articles that are intended to be discarded after a single use. That is, they are not intended to be laundered or otherwise restored or reused.

As used herein, the term "feminine hygiene articles" refers to articles that typically can be intended for feminine use, such as, e.g., absorbent articles, such as, e.g., sanitary napkins, liners, tampons, interlabial articles, incontinence articles; and pessaries.

As used herein, the term "tampon" refers to any type of absorbent structure such as, e.g., an absorbent mass, that can be inserted into the vaginal canal or other body cavity for the purpose of, such as, e.g., absorbing fluid, aiding in wound healing, and/or for delivering materials, such as moisture or active materials such as medicaments. The term "tampon" can also include the combination of an absorbent structure with any type of applicator that can be associated with the absorbent structure to facilitate insertion of a tampon into the vaginal canal or other body cavity. A tampon can include any known tampon configuration such as, for example, digital tampons, tampons with traditional plunger type applicators, and/or tampons with compact applicators, such as, e.g., tampons described in U.S. Pat. Nos. 4,726,805; 4,846,802; 4,960,417; 5,087,239; 5,279,541; 6,258,075; 6,478,763; or any other tampon.

As used herein, the term "nonwoven" can refer to a web or fabric having a structure of individual fibers or threads which are interlaid, but not in a regular, repeating manner as in a woven or knitted fabric. Nonwoven webs or fabrics can be formed from many processes, such as, for example, meltblowing processes, spunbonding processes, hydroentangling processes, and bonded carded web processes.

FIG. 1 shows one embodiment of an individual package 10. The package 10 has an outer surface 11, an inner surface 12, a top 13, a bottom 14, a length (l), a width (w), a longitudinal axis (L), and a transverse axis (T). As shown in FIG. 1, the package 10 also has a first side 15 and a second side 16, and at least one of the sides can include fold 17. The package 10 can substantially enclose an absorbent article 20. As shown in FIG. 1, the package includes an opening area 18 covered by overlabel 19. In addition, the package can have at least three permanent side seals, 31, 32, and 33. In certain embodiments, overlabel 19 can have a tab 34.

In certain embodiments, the package can be formed of a multilayer material, such as, for example, the multiple component material set forth in co-pending U.S. patent application Ser. No. 12/414,885. The multilayer material has a first component and a second component. In certain embodiments, the first component of the package material can be a polymer, such as, e.g., a polymeric film, and the second component can be an absorbent material, such as, e.g., a nonwoven material.

Figure 2:
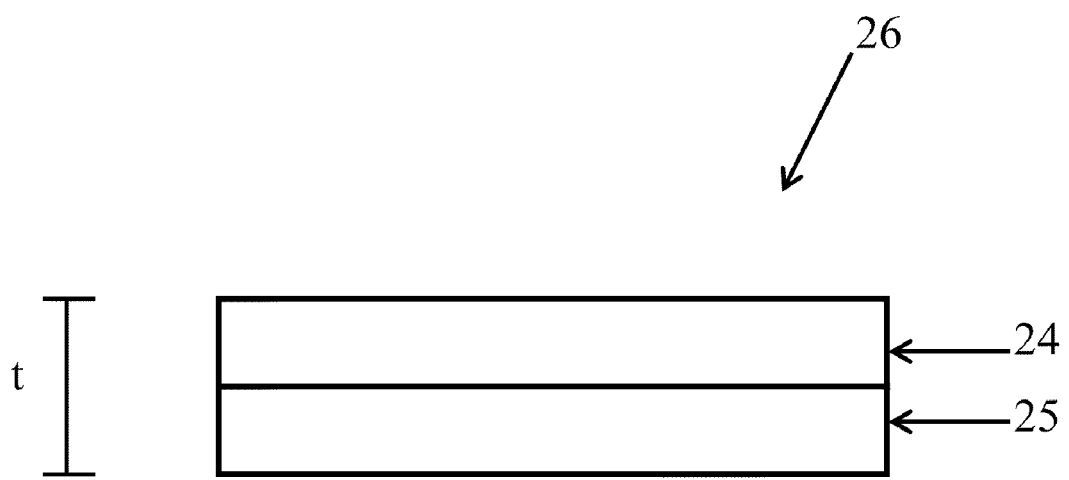
FIG. 2 is a cross-sectional view of a package material.

FIG. 2 shows a multiple component package material 26 prior to forming a package 10. As shown in FIG. 2, package material 26 can be formed from a first component 24, such as, e.g., a polymeric film, and a second component 25, such as, e.g., an absorbent material, such as, e.g., a nonwoven. In certain embodiments, the package material 26 can have a thickness (t).

The package can be formed of any suitable material, such as, for example, a polymeric film, such as, for example, polyolefins, such as, e.g., polyethylene, polypropylene, polyesters, such as, e.g., synthetic polyesters, polyamides, polyvinyl chlorides, ethylene-vinyl acetate copolymers, and/or other suitable films, a nonwoven, a formed film, a paper, or a fabric comprised of suitable material such as polyethylene, polypropylene, polyester, cellulose, rayon, cotton, super absorbent material such as polyacrylate, or combinations thereof.

In certain embodiments, the package material can be a multiple component material that can have a first component and a second component. In certain embodiments, the first component of the package material can be a polymer, such as, e.g., a polymeric film. Suitable polymers include, for example, polyolefins, such as, e.g., polyethylene, polypropylene, polyesters, such as, e.g., synthetic polyesters, polyamides, polyvinyl chlorides, ethylene-vinyl acetate copolymers, and/or other suitable films. In certain embodiments, the first component can be generally liquid repellent. In addition, or alternatively, the first component can be considered non-flushable, non-water-degradable, and/or generally insoluble in water. In certain embodiments, the outer layer can have a thickness of from about 0.0005" (~0.01 mm) to 0.003" (0.07 mm). In certain embodiments, the polymeric material can have a basis weight of less than about 50 gsm, such as, e.g., less than about 40 gsm, less than about 30 gsm, less than about 25 gsm, less than about 20 gsm, less than about 15 gsm, or less than about 10 gsm, or any other suitable basis weight. In certain embodiments, the first component can be printable, such as, e.g., printed with one or more images, such as, e.g., printed with one or more absorbency indicators, such as, e.g., printed with one or more colors corresponding to absorbency level. In certain embodiments, the first component can be amenable to high definition and/or high contrast printing.

In certain embodiments, the second component of the package material can be an absorbent material, such as, e.g, a nonwoven, a formed film, a paper, or a fabric. In certain embodiments, the second component is a nonwoven, and can include fibers comprised of polymers such as polyethylene, polypropylene, polyester, cellulose, rayon, cotton, super absorbent material such as polyacrylate, or combinations thereof. In addition, the second component can be considered non-flushable, non-water-degradable, and/or generally insoluble in water. Alternatively, in certain embodiments, the second component can be considered degradable, water soluble, and/or flushable, such as, e.g., when the second component comprises certain papers or other degradable material. In certain embodiments, the absorbent material can have a basis weight of less than about 50 gsm, such as, e.g., less than about 40 gsm, less than about 30 gsm, less than about 25 gsm, less than about 20 gsm, less than about 15 gsm, or less than about 10 gsm, or any other suitable basis weight. In certain embodiments, the absorbent material can have a basis weight of from about 10 gsm to about 40 gsm.

In certain embodiments, the package material is a multiple component material and the first component and the second component can be joined in any suitable manner to form the package material, such as, e.g., by adhesive bonding, mechanical bonding, thermal bonding, ultrasonic bonding, extrusion lamination, and the like. While complete bonding of the first component and the second component may not be necessary, in certain embodiments, the bonding should be sufficient to facilitate that the components act as a unit, e.g., bending out-of-plane together. In certain embodiments, the first component can have a surface area that is greater in size than the surface area of the second component. For example, when the first component is greater in size than the second component, the first component can be joined to itself, such as, e.g., substantially enclosing the second component, when the package material is formed into the package. Alternatively, in certain embodiments, the absorbent component is not provided on the entire inner surface of the wrapper, and is only provided on the inside of the wrapper opposite the access opening.

The package material can be any suitable thickness, such as, for example, greater than about 0.1 mm thick, such as, e.g., greater than about 0.2 mm thick, greater than about 0.3 mm thick, greater than about 0.4 mm thick, greater than about 0.5 mm thick, greater than about 0.6 mm thick, greater than about 0.7 mm thick, greater than about 0.8 mm thick, greater than about 0.8 mm thick, greater than about 0.9 mm thick, greater than about 1 mm thick, greater than about 2 mm thick, greater than about 3 mm thick, greater than about 4 mm thick, greater than about 5 mm thick, or any other suitable thickness. In addition, in certain embodiments, the package material can have a high tear resistance. In certain embodiments, the package material can be considered non-flushable, non-water-degradable, and/or generally insoluble in water.

In certain embodiments, the package is sealed around the absorbent article on three or more sides, such as, for example, with permanent seals. In addition, the package can include a fold or a permanent seal on the fourth side, such that the absorbent article is sealed within the wrapper on all sides. The package includes an opening suitable for removal of the absorbent article from the package. In certain embodiments, the opening is provided substantially or entirely on a single face of the package, such as, for example, the front face or the back face of the package. In addition, the package can have an overlabel substantially covering the opening. In certain embodiments, the overlabel can cover the entire opening. Alternatively, the overlabel can cover a portion of the opening, such as, for example, a first cut through area of the opening. In this instance, as the label is peeled back, the rest of the opening is developed as the user breaks adjoining perforations defining the opening area.

The overlabel can be at least partially releasably attached to the package, such that the overlabel can be partially or entirely removed by a user to reveal the opening and to withdraw the absorbent article from the wrapper. In certain embodiments, the overlabel can be partially permanently attached and partially releasably attached to the package. In certain embodiments, the user can grasp the overlabel and peel it at least partially back to open the package. In certain embodiments, the overlabel can be releasably and/or permanently attached to the wrapper material around the periphery of the opening, such as, for example, around about 25% of the periphery, about 50% of the periphery, about 75% of the periphery, or about the entire periphery.

In certain embodiments, the overlabel is permanently attached to the package in at least one area. For example, the wrapper can be cut, scored, or perforated to create an opening area, and the overlabel can cover all or a portion of the opening area. As the overlabel is peeled back by a user, the material within the opening area is removed by the overlabel. In certain embodiments, the opening area is scored or perforated, and the overlabel is joined to the material within the opening area. Peeling of the overlabel can then break the scoring or perforations and the wrapper material within the scored or perforated area is joined to and carried along with the overlabel such that the opening is available for access to and disposal of the absorbent article.

The opening can be provided in any suitable location, such as, for example, to provide access to one end of the absorbent article, such as, for example, one end of a tampon applicator. In certain embodiments, the opening can be provided to provide access to the withdrawal end of a tampon applicator, such as, for example, in the top third of the wrapper. Generally, the opening can be provided to provide access to the absorbent article such that cleanliness of the absorbent article is maintained during removal of the absorbent article from the wrapper.

The opening can be provided in any suitable shape, such as, for example, a circle, a crescent, an oval, a semicircle, a horseshoe, an ellipse, a hexagon, an octagon, a pentagon, a star, a triangle, a rectangle, an irregular shape, a symmetrical shape, a non-symmetrical shape, or any other suitable shape. The opening can be provided with any suitable method, such as, for example, cutting, such as, die cutting or laser cutting, scoring, such as laser scoring, or perforating, such as, mechanical perforations, or any other suitable method.

Any suitable overlabel for sealing the package can be used, such as overlabels formed from materials such as, e.g., polypropylene, polyesters, acetate, vinyl, polyethylene terephthalate, foil, wax, resin, paper, nonwoven, or any other suitable material.

The overlabel can be attached to the wrapper in any suitable manner, such as, for example, using pressure sensitive adhesives, heat activated adhesives, hot melt adhesives, solvent based adhesives, water based adhesives, glue, or any other suitable adhesive. The overlabel can be any suitable thickness, such as, for example, from 1.5 mil to 2.0 mils (0.0015"-0.002") in thickness. In certain embodiments, the overlabel and wrapper material can be provided such that the overlap has an adhesive peel force of greater than about 35 g, about 50 g, about 75 g, or any other suitable peel force after placement of the overlabel on the wrapper. The overlabel must be removable from the wrapper surface, such as, for example, peelable, such that the overlabel can be partially or entirely removed by a user to access the absorbent article within the wrapper.

In certain embodiments, at least a portion of an absorbent article and/or related material will need to be disposed after use. The user can place the used article into the package for disposal. For example, in certain embodiments, the package can include a pocket and the pocket can act to contain at least a portion of the used absorbent article or portion thereof. In certain embodiments, the overlabel can be refastened over the used article once it is placed into the package for transportation and/or disposal, such as, e.g., to provide increased discretion and cleanliness during transportation and/or disposal. Alternatively, or in addition, the package can be configured such that it can be wrapped around the used article to facilitate disposal. In certain embodiments, the overlabel can be used to seal the wrapper around the used article.

The package can be formed in any suitable configuration. Suitable configurations can include, for example, a tampon package, a sanitary napkin release paper wrapper, such as, for example, a tri-fold or bi-fold configuration, an incontinence pad wrapper, a liner package, or any other suitable configurations.

The package can be constructed in any suitable manner, such as, e.g., constructed of one connected piece of package material or constructed from multiple pieces of material sufficiently joined together such that it substantially acts as one connected piece of package material. In certain embodiments, the package can be formed by closing the package material via heat-sealing onto itself before and/or after wrapping the absorbent article. In addition, or alternatively, the package can be glued, embossed, crimped, sewed, stitched, entangled, mechanically interlocked, cold pressure welded, ultrasonic bonded, and/or otherwise bonded or sealed.

Figure 3:
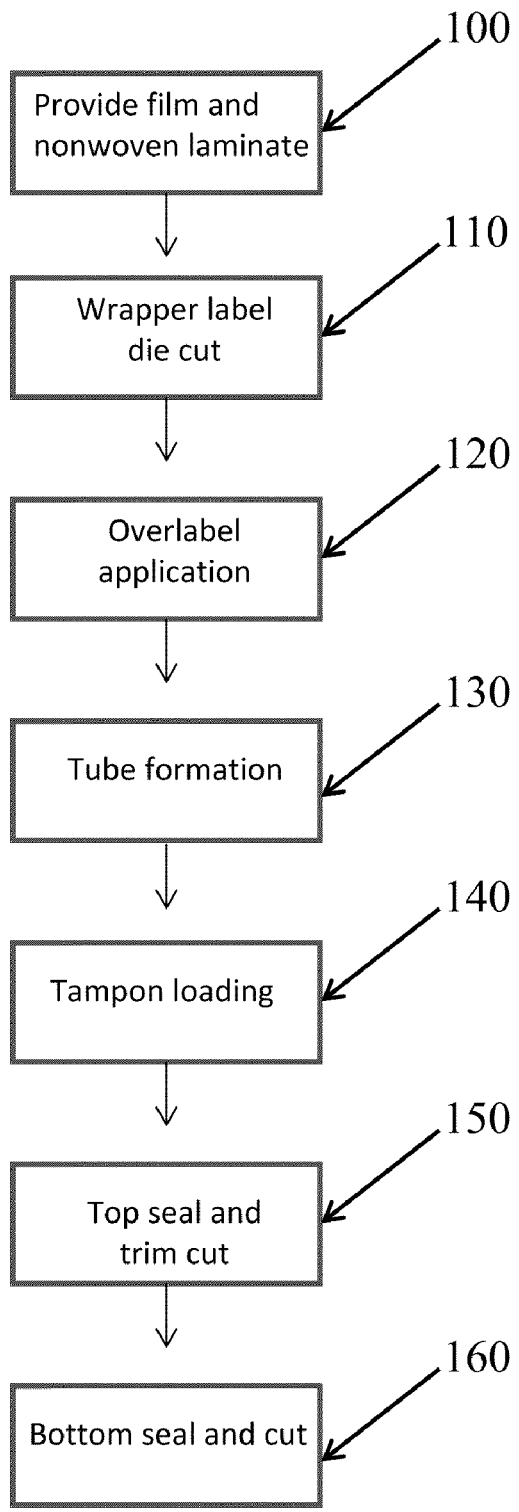
FIG. 3 is a flow diagram of a method of making an individual package.

In certain embodiments, the wrapper can be formed as shown in steps 110-160 of FIG. 3. For example, the wrapper material can be provided, the wrapper label is then cut, scored, or perforated to provide the opening 110, and the overlabel is applied substantially covering at least a portion of the cut, scored, or perforated region 120. Next, a tube is formed 130, such as, for example, by folding the wrapper material longitudinally and providing a permanent side seal opposite the fold. Next, the tampon is loaded 140 through the top or bottom of the wrapper and the top is permanently sealed and cut 150, and the bottom end is permanently sealed and cut 160.

When a multiple component material is used, the multiple component material can be formed prior to construction of the package, such as, for example, on the line with construction of the package, at a separate location from the construction of the package, or in any other suitable order or configuration. Generally, the multiple component material is formed by joining the first component and the second component to form the multiple component material, such as, for example, by using an adhesive.

In certain embodiments, a multiple component material is formed offline and provided as shown in FIG. 3 in the form of a film and nonwoven laminate 100. The wrapper label is then die cut to provide the opening 110, and the overlabel is applied substantially covering the die cut region 120. Next, a tube is formed 130, such as, for example, by folding the wrapper material longitudinally and providing a permanent side seal opposite the fold. Next, the tampon is loaded 140 through the top or bottom of the wrapper and the top is permanently sealed and cut 150, and the bottom end is permanently sealed and cut 160.

In certain embodiments, a multiple component material is formed online and then formed into the wrapper as shown in steps 110-160 of FIG. 3. For example, in certain embodiments, the film component can be unwound, adhesive applied, and the nonwoven material joined to the film component to form the film and nonwoven laminate 100. The wrapper label is then die cut to provide the opening 110, and the overlabel is applied substantially covering the die cut region 120. Next, a tube is formed 130, such as, for example, by folding the wrapper material longitudinally and providing a permanent side seal opposite the fold. Next, the tampon is loaded 140 through the top or bottom of the wrapper and the top is permanently sealed and cut 150, and the bottom end is permanently sealed and cut 160.

In certain embodiments, the feminine device can be a tampon. The tampon can include a pledget that can include one or more absorbent materials. The materials for the tampon can be formed into a fabric, web, or batt that is suitable for use in the tampon by any suitable process such as, for example, airlaying, carding, wetlaying, hydroentangling, or other known techniques.

The pledget can be constructed from a wide variety of liquid-absorbing materials commonly used in absorbent articles. Such materials include, for example, rayon (such as GALAXY rayon (a tri-lobed rayon) or DANUFIL rayon (a round rayon), both available from Kelheim Fibres GmbH of Kelheim, Germany), cotton, folded tissues, woven materials, nonwoven materials, synthetic and/or natural fibers or sheeting, comminuted wood pulp, which is generally referred to as airfelt, foams, or combinations of these materials. Examples of other suitable materials include: creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these. Additionally, superabsorbent materials, such as superabsorbent polymers or absorbent gelling materials can be incorporated into the tampon.

The pledget can have any suitable shape, size, material, or construction prior to compression and/or shaping. For example, the pledget can include a rolled, tubed, or flat construction of an absorbent that can be a circle, an oval, a semi-circle, a triangle, a chevron shape, an H shape, a bow-tie shape, or any other suitable shape, such as, e.g., shapes described in, for example, U.S. Pat. Nos. 3,738,364; 5,911, 712; 6,740,070; 6,887,266; and 6,953,456.

In certain embodiments, all or a portion of the tampon can be compressed into a substantially cylindrical configuration, however, other shapes are possible. These can include shapes having a cross section or cross-section element that can be described as rectangular, triangular, trapezoidal, semi-circular, hourglass, or other suitable shapes. In certain embodiments, the tampon can have a radially compressed rolled construction. The tampon can be constructed by rolling and radially compressing a pledget. In addition, or alternatively, the tampon can include an asymmetric insertion end, such as, e.g., tampons disclosed in U.S. patent application Ser. Nos. 11/526,041 and 11/525,513.

A tampon can comprise one or more overwraps, such as, e.g., one or more overwraps attached to the compressed tampon. The overwrap can be any suitable material, such as, for example, rayon, cotton, bicomponent fibers, polyethylene, polypropylene, other suitable natural or synthetic fibers known in the art, and mixtures thereof. In certain embodiments, the tampon can comprise an overwrap material that substantially encloses the compressed tampon. In certain embodiments, the overwrap can extend from the withdrawal end of the tampon.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An individually packaged absorbent article comprising:
an absorbent article;
a package enclosing the absorbent article, the package having an outer surface and an inner surface disposed opposite the outer surface, the package comprising a package material having a first component that is a polymeric film;
the package having two opposing faces, and an opening area, the opening area being provided substantially on a face of the package, the package having an overlabel at least partially covering the opening area,
wherein the package material has a second component that is an absorbent material, the first component and the second component being joined together to form the package material, wherein the package material is oriented such that the first component forms the outer surface of the package and the second component forms the inner surface of the package.

2. The individually packaged absorbent article of claim 1, wherein the opening area is defined by cuts, scores, or perforations.

3. The individually packaged absorbent article of claim 1, wherein the package material has a thickness greater than about 0.1 mm.

4. The individually packaged absorbent article of claim 1, wherein the second component has a basis weight less than about 50 gsm.

5. The individually packaged absorbent article of claim 1, wherein the package material is water insoluble.

6. The individually packaged absorbent article of claim 1, wherein the package is reclosable.

7. The individually packaged absorbent article of claim 1, wherein the absorbent article is a tampon, a sanitary napkin, an interlabial pad, a pessary, or an incontinence pad.

8. An individually packaged absorbent article comprising:
an absorbent article;
a package enclosing the absorbent article, the package having an outer surface and an inner surface disposed opposite the outer surface, a periphery, a longitudinal axis, a transverse axis, a length measured parallel to the longitudinal axis, a width measured parallel to the transverse axis, a top, a bottom, and two sides;
the package comprising a package material having a first component that is a polymeric film; and
wherein the package has permanent seals at the top, bottom, and at least one side, the package having two opposing faces and an opening area, the opening area being provided substantially on a face of the package, the package having an overlabel that is positioned over the opening area and extends beyond the periphery of the opening area.

9. The individually packaged absorbent article of claim 8, wherein the package material has a second component that is an absorbent material, the first component and the second component being joined together to form the package material, wherein the package material is oriented such that the first component forms the outer surface of the package and the second component forms the inner surface of the package.

10. The individually packaged absorbent article of claim 8, wherein the opening area is defined by cuts, scores, or perforations.

11. The individually packaged absorbent article of claim 8, wherein the absorbent article is a tampon, a sanitary napkin, an interlabial pad, a pessary, or an incontinence pad.

12. An individually packaged absorbent article comprising:
an absorbent article;
a reclosable package enclosing the absorbent article, the package having an outer surface and an inner surface disposed opposite the outer surface, the package comprising a package material having a first component that is a polyolefin film, and a second component that is an absorbent material, the first component and the second component being joined together to form the package material, wherein the package material is oriented such that the first component forms the outer surface of the package and the second component forms the inner surface of the package,
the package having two opposing faces and an opening area, the opening area being provided substantially on a face of the package, the package having an overlabel that is made from overlabel material distinct and separate from the package material and that at least partially covers the opening area.

13. The individually packaged absorbent article of claim 12, wherein the printed polyolefin film includes a printed absorbency identifier and the second component is a nonwoven or a formed film.

14. The individually packaged absorbent article of claim 12, wherein the opening area is defined by cuts, scores, or perforations.

15. The individually packaged absorbent article of claim 12, wherein the package material has a thickness greater than about 0.1 mm.

16. The individually packaged absorbent article of claim 12, wherein the second component has a basis weight less than about 50 gsm.

17. The individually packaged absorbent article of claim 12, wherein the package material is water insoluble.

18. The individually packaged absorbent article of claim 12, wherein the package is reclosable.

19. The individually packaged absorbent article of claim 12, wherein the absorbent article is a tampon, a sanitary napkin, an interlabial pad, a pessary, or an incontinence pad.

* * * * *